(12) United States Patent
Schönborn et al.

(10) Patent No.: US 8,489,175 B2
(45) Date of Patent: Jul. 16, 2013

(54) METHOD AND DEVICE FOR IMAGING AN ORGAN

(75) Inventors: Manfred Schönborn, Gerhardshofen (DE); Rudolf Heimberger, Würzburg (DE); Herbert Kemeth, Hausen (DE); Winfried Lurz, Fürth (DE); Frank Grasser, Eggolsheim (DE)

(73) Assignee: Siemens Aktiengesellschaft, München (DE)

( * ) Notice: Subject to any disclaimer, the term of this patent is extended or adjusted under 35 U.S.C. 154(b) by 1419 days.

(21) Appl. No.: 11/581,716

(22) Filed: Oct. 16, 2006

(65) Prior Publication Data

US 2007/0100227 A1     May 3, 2007

(30) Foreign Application Priority Data

Oct. 17, 2005 (DE) .......................... 10 2005 049 603

(51) Int. Cl.
*A61B 5/05* (2006.01)

(52) U.S. Cl.
USPC .............................. 600/428; 600/425; 378/11

(58) Field of Classification Search
USPC ................ 600/425, 428, 431, 509; 382/8, 95; 378/11–16
See application file for complete search history.

(56) References Cited

U.S. PATENT DOCUMENTS

| | | | |
|---|---|---|---|
| 6,324,254 B1 | 11/2001 | Pflaum | |
| 6,370,217 B1 | 4/2002 | Hu et al. | |
| 7,027,855 B2* | 4/2006 | Okerlund et al. | 600/509 |
| 2002/0126794 A1* | 9/2002 | Rasche et al. | 378/8 |
| 2003/0069499 A1* | 4/2003 | Lienard et al. | 600/431 |
| 2004/0042581 A1 | 3/2004 | Acharya | |
| 2005/0058248 A1* | 3/2005 | Klingenbeck-Regn | 378/95 |
| 2006/0133564 A1* | 6/2006 | Langan et al. | 378/8 |
| 2006/0133567 A1 | 6/2006 | Florent | |

FOREIGN PATENT DOCUMENTS

| | | |
|---|---|---|
| DE | 103 36 278 A1 | 3/2005 |
| JP | 2004523318 A | 8/2004 |
| JP | 2005052653 A | 3/2005 |

\* cited by examiner

*Primary Examiner* — James Kish
*Assistant Examiner* — Christopher Cook

(57) ABSTRACT

The invention relates to a method and device for imaging a cyclically moving organ of a human or animal body, with a device supported such that it can be rotated at an angular velocity around the body recording images of the organ from different angle positions, with the angular velocity being modulated with a reference signal representing the movement phase of the organ. During the rest phase of the organ images of the organ are recorded at nominal angular speed. In the movement phase of the organ the device is slowed down, turned back and accelerated again such that on entry into the next rest phase the device records images for the next angle range at nominal angular velocity without major angle gaps in respect of the previous angle range, to generate the most complete data record possible.

17 Claims, 2 Drawing Sheets

METHOD AND DEVICE FOR IMAGING AN ORGAN

CROSS REFERENCE TO RELATED APPLICATIONS

This application claims priority of German application No. 10 2005 049 603.2 filed Oct. 17, 2005, which is incorporated by reference herein in its entirety.

FIELD OF THE INVENTION

The invention relates to a method for imaging an organ and a device for implementing the method.

BACKGROUND OF THE INVENTION

A wide range of minimally invasive methods, for example x-ray methods, for imaging an organ are known in modern medicine. The object of these methods is essentially to obtain comprehensive knowledge about the respective organ and its state without opening up the body. In a known application for example a C-arm of an x-ray device with an x-ray tube and an x-ray detector is rotated at constant rotation speed or angular velocity o through an angle of 300 degrees for example around a patient, generally about the longitudinal axis of the body. Instead of just a local view through a catheter using a camera, etc. such imaging methods and a corresponding device can be used to acquire a number of individual recordings of the organ in question from different spatial directions, on the basis of which three-dimensional images or other representations, such as any sections in particular, can ultimately be produced. Such methods can be used to examine the cardiac muscles and coronary vessels for example without a catheter.

For a 3D reconstruction however only the images that show the organ in the same respective state can be used. In a preferred and extremely important application, the recording of the heart, the filling phase or diastole is selected as the representation state, being a relative rest phase of the heart. In the case of a living human being this rest phase lasts for less than 200 milliseconds even in a rest position during relaxation. During recording however only a few projections can be collected for 3D reconstruction and modeling in a time window in the above-mentioned cardiac rest phase. The data collected outside the recording time window or outside the cardiac rest phase of relevance to the examination respectively cannot be used for imaging because of the movement of the heart. Such data losses result in large gaps in the projection angle space and therefore an incomplete representation base for the organ as a whole. Interpolations can perhaps be made with relatively uncertain assumptions within these representation gaps. A similar problem also arises with other organs, the form and/or position of which changes over time. However in order to keep the overall radiation load low, where the x-ray tube is in constant operation, the recording device cannot rotate at any slow rotation speed that may be required to obtain as many recordings as possible from different spatial directions at favorable recording times. Nor is it possible for a measurement to be repeated any number of times for the same reason.

It is therefore proposed in U.S. Pat. No. 6,324,254 B1 for recording a rhythmically moving vessel that the C-arm be moved at the slowest possible rotation speed, preferably less than 2 degrees per second, but taking individual image recordings, triggered by the vessel movement or an organ movement causing the vessel movement. In other words radiation is only emitted from the x-ray tube and a recording is only taken at specific times, while the C-arm moves around the patient at the slowest possible constant speed. The constant rotation speed is hereby established before measurement, preferably as a function of the frequency of the rhythmic vessel or organ movement, to ensure that a minimum number of recordings can be generated during a measurement. However this procedure has the disadvantage that the measurement takes a relatively long time. During this time it has to be ensured that the patient lies absolutely still. Even minimal position changes can cause the measurement to be impaired.

A similar method is proposed in U.S. Pat. No. 6,370,217 B1 for the measurement of a periodically moving object using a computed tomograph. During a measurement using such a computed tomography system the x-ray tube rotates at very high speed, for example at a speed in the order of approximately 1 second per rotation, a number of times around the patient. In order always to record the cyclically changing object in the same state in this process, there is also a control system here, triggered by the movement cycle, for when the x-ray tube emits short bursts of x-ray radiation to take individual recordings. Here too a constant rotation speed is preferably established before measurement as a function of the frequency of the rhythmic vessel or organ movement. The rotation speed is thereby adjusted such that where possible recordings can be generated from all spatial directions during a measurement. This method cannot however be used for a measurement with a C-arm or similar recording facilities, as, unlike with the significantly more complex structure of a computed tomography device, with such a relatively simple recording device the x-ray tube and detector cannot move at any speed and frequency around the patient. Generally only a rotation angle of maximum 300 degrees is available.

In the unexamined German application DE 103 36 278 A1 a method is disclosed for imaging an organ of the human or animal body by means of a recording device rotating through an angle, wherein the rotation speed of the rotating recording device is modulated as a function of a reference signal, which represents a current movement state of the organ to be imaged. Additionally or alternatively the measuring interval, with which the organ is recorded during the rotation, is adjusted by means of the reference signal to the duration of the movement cycle of the organ to be imaged. A corresponding device for implementing such a method is also described. One disadvantage of this method is that either angle ranges are passed through, for which no recordings are taken, or an acceleration phase of the recording device occurs at the start and end of each cycle.

SUMMARY OF THE INVENTION

The object of the invention is therefore to provide a generic method for imaging an organ and a generic method for implementing the method, allowing the most complete data record possible to be recorded with little time outlay.

The part of the object relating to the method is achieved with a generic imaging method, in that the recording device is rotated during a first movement phase, with images of the organ being recorded from angle positions of a first angle range at a nominal angular velocity and that during a second movement phase following directly after the first movement phase the recording device is slowed down, turned back and accelerated again, such that the recording device reaches nominal angular velocity at the latest at the start of a first movement phase following directly after the second movement phase, at the end of the first angle range.

The overall angle range of 300 degrees for example, covered during the examination, is made up of a number of angle ranges, of 10 degrees each for example, which are covered during the respective first movement phases of the organ. Each position of an angle range, in which an image is recorded, is referred to as an angle position. While the for example 10 degrees of an angle range are being covered, with images being recoded in the process, the recording device rotates at a constant angular velocity, referred to here as the nominal angular velocity. The nominal angular velocity has quantity and direction and is therefore a signed variable.

For time reasons it is advantageous not to duplicate recording for an angle position and this is particularly significant at the transition between two angle ranges. Alternatively there can be an overlap of angle positions, as the uncertainty increases toward the end of the first movement phase that unsuitable images might be recorded for an imaging process, as the duration of the first phase of movement of the organ can be subject to fluctuations. The method therefore allows a quasi-continuous acquisition of the overall angle range at a nominal angular velocity of the recording device.

In one advantageous embodiment of the invention the immediately adjacent angle positions in each instance differ by a constant differential angle. This does not exclude more than one recording being taken at one angle position.

The constant nature of the differential angle allows simplified evaluation of the images obtained and optionally also their conversion to a spatial representation.

In a further advantageous embodiment of the invention the differential angle is adjusted by way of an image recording rate of the device. Increasing or reducing the image recording rate, in other words the images recorded per time interval, causes the differential angle to change for the angle positions at constant nominal angular velocity. This makes it possible to control the accuracy of the result and the radiation dose for the patient.

In an alternative embodiment of the invention the differential angle is adjusted by way of the nominal angular velocity. A predeterminable nominal angular velocity allows the examination time to be reduced at for example a constant image recording rate, as a larger angle range can be covered with the recording device in a first movement phase. On the other hand it also allows the differential angle between adjacent angle positions to be determined. Ideally the highest possible nominal angular velocity is always selected and the differential angle is determined by way of the image recording rate. This ensures the shortest possible examination time and allows imaging accuracy to be controlled by way of the image recording rate.

In a preferred embodiment of the invention the rotatable recording device is used to image a beating heart and the angular velocity is modulated on the basis of a reference signal representing the heartbeat. The periodic movement of a heart can be acquired very effectively with the inventive method, as the cardiac rest phases, which represent the first movement phases, which are suitable for imaging purposes, can be acquired very effectively using the method.

The angular velocity is advantageously modulated such that the recordings are always taken at the same nominal angular velocity in the cardiac rest phase. During the heartbeat the recording device is slowed down, turned back and accelerated again according to the invention such that images can again be recorded at nominal angular velocity in the next cardiac rest phase.

It proves to be advantageous, when examining the heart, for an ECG (electrocardiogram) signal to be measured to determine a reference signal. Depending on the organ for which the examination is to be carried out, a very wide range of signals can be used. Alternatively or additionally the pulse of the patient and/or ultrasound signals, etc. can be used.

In an advantageous variant of the invention the duration of the first movement phase is adjusted to the duration of the movement cycle of the organ to be imaged, the length of which is averaged over a number of movement cycles. The duration of the first movement phase, in other words the measuring period is therefore adjusted to the movement cycle of the organ to be imaged on the basis of a reference signal or image recordings already taken.

A sliding mean of the cycle duration can for example be calculated, preferably even beforehand, over a certain number of movement cycles. The measuring period can therefore be specified for example as percentage parts of the cycle duration. If it is established based on the reference signal that the cycle duration changes during recording, synchronous adjustment of the measuring period can take place. Alternatively information about the movement phase of the organ can be forwarded to a controller in real time based on the reference signal, said controller controlling the recording device based on this information.

In a further advantageous embodiment of the invention a C-shaped arm with an x-ray source and an x-ray detector disposed opposite the x-ray source, which can be rotated at an angular velocity around the body, is used as the recording device. As C-arm x-ray devices are frequently used at present to examine patients, in particular during medical interventions, an improvement is also desirable for imaging moving organs. However the method can in principle also be used with other similar recording devices.

During the second movement phase an x-ray radiation source used to record images is advantageously deactivated or at least the intensity of the x-ray radiation is reduced. This procedure allows the x-ray load to be kept as low as possible for the patient. As an alternative to deactivating the x-ray radiation source, an absorber can be provided to absorb the x-ray radiation and this can be disposed during the second movement phase such that the radiation load for the patient is negligibly low. This protects both the x-ray source and the patient.

The x-ray radiation is preferably reduced by deactivation and/or absorbers with the last recording and is ready for use again to record the first image after further acceleration of the recording device to nominal angular velocity. This effectively reduces the overall radiation load for the patient even with just one passage of the device according to the inventive method.

When acquiring arrhythmia or fluctuations over time in the execution of movement phases or movement cycles of the organ, the start point and/or duration of the first movement phase is/are preferably adjusted. This allows a phase displacement between the measuring point and/or period and the first movement phase of the organ to be identified and eliminated at an early stage. This reduces the number of recordings recorded in the second instead of the first movement phase of the organ due to phase displacement.

The images recorded in the second movement phase of the organ cannot be used to image the organ and can be selected at the end of the examination in a post-processing step, in order not to falsify the result or make it useable by interpolation. This measure is expedient in so far as all the image data determined during the measurement in one passage is generally buffered anyway, such that it is available in any case for post-processing.

In a further advantageous embodiment of the invention at least one contrast agent is fed to the body. In order to make corresponding topologies visible, for example in or on the heart, it may be necessary to feed in contrast agents. Preferably only the amount of contrast agent required to acquire the examined structure is fed to the patient. It is particularly advantageous in this process to feed in the contrast agent in a single dose before recording the first image. The contrast agent fed in is sufficient to carry out the examination as it takes place in a continuous manner.

The part of the object relating to the device is achieved with a generic imaging device in that a measuring facility is present to determine a reference signal, which represents the current movement state of the organ to be imaged, and a control facility, which controls the drive facility such that the recording device can be rotated during a first movement phase, it being possible to record images of the organ from angle positions of a first angle range at a nominal angular velocity, and that during a second movement phase following directly after the first movement phase the recording device can be slowed down, turned back and accelerated again, such that the recording device reaches nominal angular velocity at the latest at the start of a first movement phase following directly after the second movement phase, at the end of the first angle range.

The inventive control facility or its components can preferably be implemented predominantly in the form of software in a conventional, computer-assisted processor of a controller of the recording device. This means that it is possible also to implement the method described above at a later stage, also in the form of a computer program product, in particular an update, in existing devices.

BRIEF DESCRIPTION OF THE DRAWINGS

The inventive method and device are described in more detail below with reference to an exemplary embodiment. In the figures

DETAILED DESCRIPTION OF THE INVENTION

Figure 1:
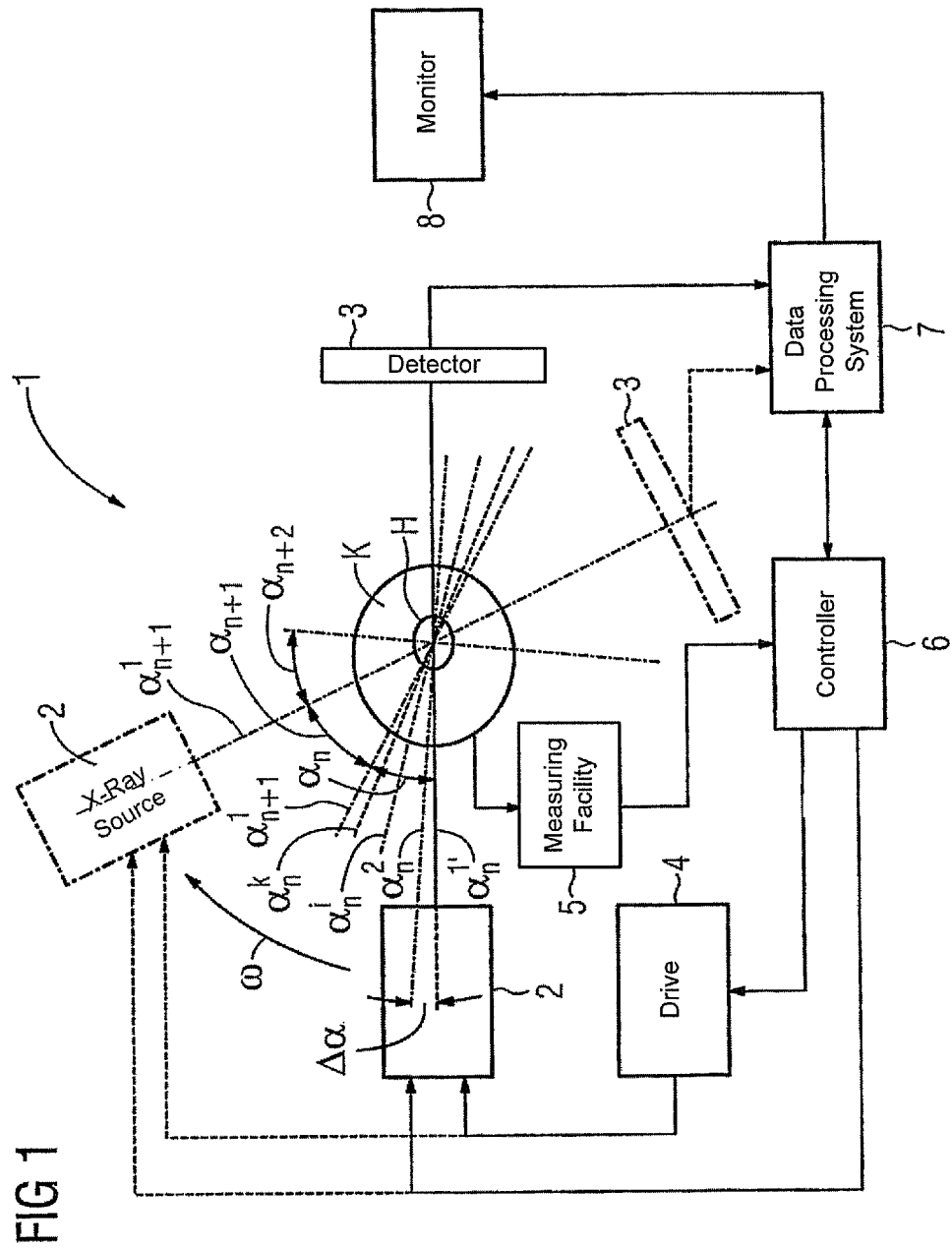
FIG. 1 shows an inventive imaging device.

The inventive imaging device shown in FIG. 1 comprises a recording device 1 in the form of a C-arm, to whose opposing ends an x-ray source 2 and an x-ray detector 3, e.g. a flat panel detector, are attached. An organ to be imaged, in this instance the heart H, of a human or animal body K, which is disposed on an examination table (not shown) and is located centrally between the x-ray source 2 and the x-ray detector 3. The imaging device has a drive 4, which can be used to rotate the recording device 1 at an angular velocity $\omega$ around the body K.

During imaging the recording device 1 passes through angle ranges $\alpha_n$, where n=1, 2, 3, . . . . In FIG. 1, for reasons of clarity, only three different angle ranges are shown, namely an angle range $\alpha_n$, a next adjacent angle range $\alpha_{n+1}$ and a next but one angle range $\alpha_{n+2}$. The sum of the angle ranges $\alpha_n$ gives the overall angle range of 300 degrees of the recording device 1. In every angle range $\alpha_n$ the recording device 1 records images from different angle positions $\alpha_n^i$, where i=1, 2, . . . , k, the first two angle positions $\alpha_n^1$ and $\alpha_n^2$ and the last angle position $\alpha_n^k$ being shown in FIG. 1 for the angle range $\alpha_n$. Further angle positions exist between $\alpha_n^2$ and $\alpha_n^k$. The number k of angle positions $\alpha_n^i$ is predetermined by the nominal angular velocity $\omega_N$ and the image recording rate of the recording device 1. This applies similarly to further angle ranges, e.g. $\alpha_{n+1}$, $\alpha_{n+2}$, for which the respective first angle positions $\alpha_{n+1}^1$ or $\alpha_{n+2}^1$ are specified.

The differential angle $\Delta\alpha$ refers across all angle ranges to the angle interval between directly adjacent angle positions, e.g. $\alpha_n^2 - \alpha_n^1$. The differential angle $\Delta\alpha$ can be predetermined by the image recording rate at a defined nominal angular velocity $\omega_n$ of the recording device 1, which is selected to be as high as possible, e.g. 40 degrees per second. The number of angle positions k in an angle range $\alpha_n$ with a constant differential angle $\Delta\alpha$ between adjacent angle positions essentially influences the quality of the spatial representation of the organ H.

A measuring facility 5, in this instance an ECG (electrocardiogram) device is used to acquire the movement cycle of the heart H and to determine from it a duration for a first movement phase $T_1$ suitable for imaging and for a second movement phase $T_2$ unsuitable for imaging. The repeated first and second movement phases $T_1$ and $T_2$ are referred to below for the nth movement repetition as $T_1^n$ and $T_2^n$ and for the n+1th movement repetition as $T_1^{n+1}$ and $T_2^{n+1}$, etc. The duration of the respective movement phase $T_1$ or $T_2$ can be determined beforehand, being averaged over a plurality of movement cycles.

The duration of the first movement phases $T_1$ essentially determines the size of the angle range that can be passed through at a predetermined nominal angular velocity $\omega_N$, through which the recording device 1 can be rotated at nominal angular velocity $\omega_N$. However the information about the movement of the heart H from the ECG device is advantageously evaluated in real time by a controller 6 in conjunction with a data processing system 7, which controls the recording device 1 and the drive 4 on the basis of this information.

The recorded images are fed to the data processing system 7, where they are stored and further processed. For example by aligning ECG data and recording points of images it is possible to select and/or correct images recorded in the second movement phase. The data processing system 7 also carries out reconstruction for the spatial representation of the heart H and forwards the image data thus determined to a monitor 8 to be viewed by medical personnel.

Figure 2:
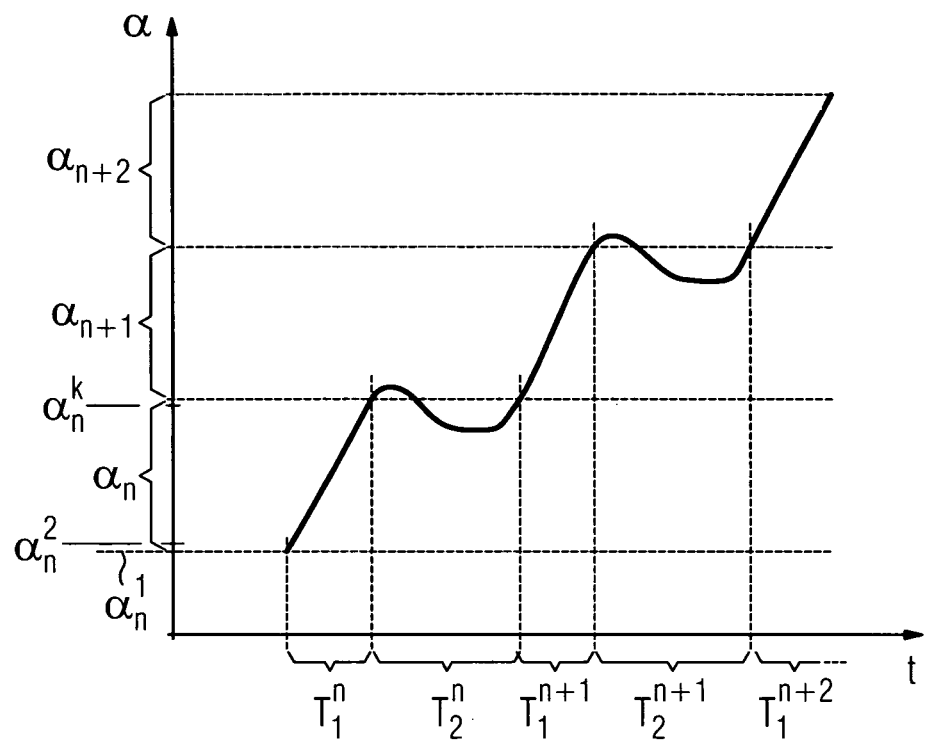
FIG. 2 shows a diagram of segments of the pattern of the angle of the recording device as a function of time when implementing the inventive method

The diagram shown in FIG. 2 shows a constant increase in the angle a of the recording device over time t during the period of the respective first movement phases $T_1$. The increase represents the nominal angular velocity $\omega_N$, which should be selected to be as high as possible in respect of the period of the respective first movement phases $T_1$ predetermined by the organ (H).

During this time period $T_1$ images of the organ (H) are recorded at a predetermined image recording rate, which determines the angle positions $\alpha_n^i$. Conversely the image recording rate can similarly be determined by way of the desired angle positions $\alpha_n^i$. At the end of the respective first movement phase $T_1$ the controller 6 stops the imaging process and slows down the recording device 1 by activating the drive 4. The inertia of the recording device 1 means that an abrupt stop is not possible.

This can be seen at the start of the intervals of the respective second movement phases $T_2$ in the diagram. The increase drops off until it reaches the value zero. This represents the reversal point of the slowed recording device 1. The recording device 1 is then rotated by the drive 4 in the direction counter to the original rotation direction. This is shown in the diagram by the decrease in the angle $\alpha$ over time t. The unit is turned back in a controlled manner by the controller 6 within the respective second movement phases $T_2$ until the drive 4 can accelerate the recording device 1 back to nominal angular velocity $\omega_N$ on the turned back angle sub-range. This position is reached at the second reversal point of the recording device 1, shown in the diagram as a local minimum of the angle $\alpha$ within the interval of the respective second movement phase $T_2$.

The reference signals of the ECG device 5 allow the drive 4 to be controlled by the controller 6 such that when the organ (H) enters the next first movement phase $T_1$ the recording device 1 has nominal angular velocity $\omega_N$ at the end of the previously recorded angle range $\alpha_n$ and therefore enters the next angle range $\alpha_{n+1}$ at nominal angular velocity $\omega_N$.

At the same time as the heart H enters the respectively next first movement phases $T_1$ image recording is restarted, being previously initiated by the controller 6. As in the case of the heart H the duration of the first movement phases $T_1$ is significantly shorter than the duration of the second movement phase $T_2$, there are different options for turning back the recording device 1. Turning back can take place segment by segment at constant angular velocity $\omega$ or as a permanently accelerated or slowed movement.

The extent of acceleration or negative constant angular velocity $\omega$ of the recording device 1 can be selected such that the dwell time of the recording device 1 at the reversal points varies. The recording device 1 could either dwell in a dwelling position for a dwell period preferably at the second reversal point, as shown in FIG. 3, or can be moved more slowly such that no break in the rotation of the recording device 1 is necessary, in order to be able to measure respective first movement phases $T_1$ again at nominal angular velocity $\omega_N$.

Figure 3:
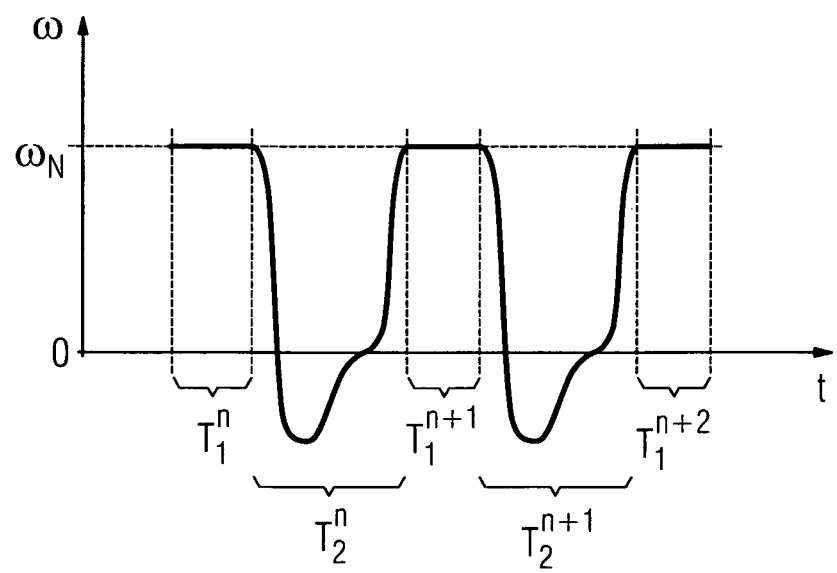
FIG. 3 shows a diagram of segments of the pattern of the angular velocity of the recording device as a function of time when implementing the inventive method, all the above being illustrated schematically.

To clarify the movement sequence, FIG. 3 shows the angular velocity $\omega$ of the recording device 1 as a function of the time t. In the respective first movement phases $T_1$ the recording device 1 has a constant nominal angular velocity $\omega_N$ and passes at this nominal angular velocity $\omega_N$ through an angle range $\alpha_n$. When the heart H enters the respective next second movement phase $T_2$, the recording device is slowed down, in other words the angular velocity $\omega$ is reduced to a value zero, and becomes negative, in other words the direction of the angular velocity $\omega$ is now in the direction counter to the original nominal angular velocity $\omega_N$.

The recording device 1 is therefore turned back to the direction counter to the original direction. The recording device 1 reaches a reversal point in the counter direction. Associated with this is a decrease in the amount of negative angular velocity $\omega$ to zero. The angle $\alpha$ of the reversal point is generally further back than the last angle position $\alpha_n^k$ of the previously recorded angle range $\alpha_n$. From this reversal point the recording device 1 is accelerated such that the nominal angular velocity $\omega_N$ reached in the previous angle range $\alpha_n$ is reached again at the latest when the recording device 1 enters the next angle range $\alpha_{n+1}$ at the start of the next first movement phase $T_1^{n+1}$ of the heart H.

Alternatively data redundancy can be generated in that image recording takes place at nominal angular velocity $\omega_N$ before entry into the next angle range $\alpha_{n+1}$ and therefore images are also recorded from angle positions $\alpha_n^i$ of the angle range $\alpha_n$ during the respective first movement phases $T_1$, by means of which defective images can be replaced during post-processing.

It is possible for the overall angle range of 300 degrees of the recording device 1 to be utilized either only with the forward travel or with the forward and backward travel. It is advantageous when using forward and backward travel, that it is not necessary to wait until the recording device 1 moves back to a zero position, with unrestricted access to the patient being available again immediately after the examination. Such a method can be implemented without further time losses during the examination, in that during forward travel every second first movement phase of the organ is used for recording and during backward travel recordings are taken for precisely those angle ranges, which were passed over without recording during forward travel. It would therefore be possible to improve the completeness of a data record by the factor 2 even with methods as claimed in the prior art.

During the examination the recorded images are fed by the detector 3 to a data processing system 7 and backed up there. Post-processing can take place, for example in the event of arrhythmia of the heart (H). The ECG signal of the ECG device 5 acquired over time and the image recording points can also be aligned, to find image recording points which cannot be assigned to any first movement phase $T_1$. These are selected and are not used to reconstruct the spatial representation of the heart (H), as they have a falsifying influence on the result of the reconstruction. After the end of the reconstruction the spatial representation thus determined is output on a monitor 8.

The invention claimed is:

1. A method for recording a plurality of images of an organ of a live body cyclically having a first movement phase suitable for recording and a second movement phase not suitable for recording, comprising:
   determining a reference signal representing a current movement phase of the organ;
   modulating an angular velocity of a recording device based on the reference signal, wherein the recording device comprises an x-ray source/detector system;
   rotating the recording device at a nominal angular velocity during the first movement phase in a first angle range at a first direction, the nominal angular velocity is selected based on an imaging rate of the recording device;
   recording the images of the organ from a plurality of different angle positions in the first angle range during the first movement phase;
   determining a differential angle with an image recording rate at the nominal angular velocity of the recording device selected at a rate as high as possible to allow for a quasi-continuous acquisition of images around an overall angle range comprised of the different angle positions;
   differing by the differential angle the plurality of different angle positions adjacent to each other;
   adjusting the differential angle by way of an image recording rate of the recording device;
   reducing the nominal angular velocity of the recording device during the second movement phase in the first angle range followed directly after the first movement phase in the first angle range;
   rotating the recording device at a direction opposite the first direction during the second movement phase in the first angle range; and
   accelerating the recording device at the first direction to reach the nominal angular velocity at an end of the first angle range that is a start point of the first movement phase in a second angle range followed directly after the second movement phase in the first angle range such that images recorded in the second angle range are done so at the nominal angular velocity used during the first movement phase.

2. The method as claimed in claim 1, wherein determining a reference signal representing a current movement phase of the organ further comprises determining a reference signal representing the first or the second movement phase.

3. The method as claimed in claim 1, wherein the organ is a beating heart of the live body and wherein modulating the angular velocity further comprises modulating the angular velocity of the recording device based on the reference signal representing a heartbeat.

4. The method as claimed in claim 3, further comprising measuring an ECG signal to determine the reference signal.

5. The method as claimed in claim 1, wherein a duration of the first movement phase is adjusted to a duration of a movement cycle of the organ averaged over a plurality of movement cycles.

6. The method as claimed in claim 5, wherein the start point or the duration of the first movement phase is adjusted when acquiring an arrhythmia or a fluctuation over time in a plurality of movement phases or in the movement cycles of the organ.

7. The method as claimed in claim 1, wherein a contrast agent is injected into the live body.

8. A medical image device that records a plurality of images of an organ of a live body cyclically having a first movement phase suitable for recording and a second movement phase not suitable for recording, comprising:
 a recording device;
 a measuring device configured to determines a reference signal representing a current movement phase of the organ;
 a drive device configured to rotates the recording device around the live body based on the reference signal; and
 a control device configured to control and activate the drive device to perform:
 rotating the recording device to record the images of the organ from a plurality of different angle positions in a first angle range during the first movement phase at a nominal angular velocity at a first direction, the nominal angular velocity is selected based on an imaging rate of the recording device,
 determining a differential angle with an image recording rate at the nominal angular velocity at a rate as high as possible to allow for a quasi-continuous acquisition of images around an overall angle range comprised of the different angle positions,
 differing by the differential angle the plurality of different angle positions adjacent to each other,
 adjusting the differential angle by way of an image recording rate of the recording device,
 decelerating the recording device during the second movement phase in the first angle range followed directly after the first movement phase in the first angle range;
 rotating the recording device at a direction opposite the first direction during the second movement phase in the first angle range, and
 accelerating the recording device at the first direction to reach the nominal angular velocity at an end of the first angle range that is a start of the first movement phase in a second angle range followed directly after the second movement phase in the first angle range such that images recorded in the second angle range are done so at the nominal angular velocity used during the first movement phase;
 wherein the recording device comprises at least an x-ray source/detector system.

9. The medical image device as claimed in claim 8, wherein the recording device comprises a C-shaped arm with an x-ray radiation source and an x-ray radiation detector disposed opposite the x-ray radiation source and the C-shaped arm rotates around the body at the angular velocity.

10. The medical image device as claimed in claim 9, wherein the x-ray radiation source is deactivated or an intensity of x-ray radiation is reduced during the second movement phase.

11. The medical image device as claimed in claim 8, wherein the live body is a human body or an animal body.

12. The medical image device as claimed in claim 8, wherein the nominal angular velocity is predetermined.

13. The medical image device as claimed in claim 8, wherein the nominal angular velocity is constant.

14. The medical image device as claimed in claim 8, wherein the current movement phase is the first or the second movement phase.

15. The medical image device as claimed in claim 8, wherein the differential angle is determined to provide for a shortest possible activation of an imaging source from the recording device.

16. The medical image device as claimed in claim 8, further comprising deactivating an imaging ability of the recording device in between each recording.

17. The medical image device as claimed in claim 8, further comprising applying absorbers in a path of the x-ray source of the recording device to impede imagining during rotating of the recording device in the opposite direction and before further acceleration.

* * * * *